United States Patent [19]

Rafetto, Jr.

[11] Patent Number: 5,529,493
[45] Date of Patent: Jun. 25, 1996

[54] MIXING AND STORAGE ASSEMBLY FOR CERAMIC MATERIAL

[76] Inventor: Rodney F. Rafetto, Jr., 500 E. Providence Rd., Suite 5A, Aldan, Pa. 19019

[21] Appl. No.: 209,552

[22] Filed: Mar. 10, 1994

[51] Int. Cl.⁶ ................................................ A61C 1/14
[52] U.S. Cl. ................................................ 433/49; 118/268
[58] Field of Search .................. 433/25, 49; 118/264, 118/268, 270, 269; 220/187; 101/333

[56] References Cited

U.S. PATENT DOCUMENTS

| | | |
|---|---|---|
| 966,951 | 8/1910 | Raven, Jr. |
| 1,596,130 | 8/1926 | Underwood et al. .................. 118/264 |
| 1,840,777 | 1/1932 | Hunter .................................. 118/264 |
| 2,341,285 | 2/1944 | Petrullo . |
| 2,500,066 | 3/1950 | Gaunt .................................. 118/264 |
| 2,554,302 | 5/1951 | Keskitalo ............................. 222/187 |
| 2,827,012 | 3/1958 | Kesling ............................... 118/268 |
| 2,875,727 | 3/1959 | Robinson ............................ 118/268 |
| 2,914,876 | 12/1959 | Osler . |
| 3,172,356 | 3/1965 | Vosburg .............................. 101/333 |
| 3,326,180 | 6/1967 | Lofgren ............................... 118/264 |
| 3,966,094 | 6/1976 | Sheppard ............................ 222/187 |
| 4,180,159 | 12/1979 | Tanaka . |
| 4,497,275 | 2/1985 | Johnson . |
| 5,044,008 | 8/1991 | Jackson .............................. 378/168 |

FOREIGN PATENT DOCUMENTS

| | | | |
|---|---|---|---|
| 2595940 | 9/1987 | France ................................. 433/49 |
| 2640871 | 6/1990 | France ................................. 433/25 |
| 3435885 | 4/1986 | Germany ............................ 433/49 |
| 15794 | of 1894 | United Kingdom ............. 118/268 |
| 25876 | of 1913 | United Kingdom ............. 118/268 |

*Primary Examiner*—Cary E. O'Connor
*Attorney, Agent, or Firm*—Famiglio & Massinger

[57] ABSTRACT

A mixing and storage assembly for ceramic materials such as dental porcelain, comprising an open-cell foam pad disposed within a removable micro fine knit fabric sheath. The pad and surrounding sheath are together charged to a mixing and storage vessel which further contains a reservoir of water or other liquid suitable for the preparation of a workable ceramic mix. The assembly is capable of maintaining the proper moisture content of the mix during both use and storage without the frequent need for stirring or water replenishment and without the threat of supersaturation of the mix. Liquid flow from the reservoir to the substrate mix is regulated by the capillary action inherent in the pad which maintains a consistent liquid content for supply to the porcelain powder thereby retarding premature hardening due to moisture loss associated with evaporation.

12 Claims, 1 Drawing Sheet

MIXING AND STORAGE ASSEMBLY FOR CERAMIC MATERIAL

BACKGROUND OF THE INVENTION

The object invention relates to dentistry equipment, in general, and to a mixing and storage assembly for ceramic materials such as dental porcelain, in particular.

Heretofore, difficulty has been encountered in maintaining the proper moisture content of dental porcelain during its use and storage. Frequently used for dental restorative work, porcelain is a hard, white, translucent and non-porous ceramic material known for its bio-compatability and corrosion-resistant properties. Dentists and other professionals who use this material for the fabrication of dentures, pontic or crowns, for example, typically purchase it in the form of a powder to be admixed with water or other suitable liquids.

Because the workability of the mixture is a direct function of its "wetness", it is important to maintain the proper moisture content during use and storage. It is well known to those skilled in the art of dental restorative fabrication, however, that the porcelain mixture rapidly commences to harden or "set" after preparation due to water loss through evaporation. During use, it is common practice to add water or other liquid to maintain the mixture in a workable state. Failure to do so often results in mixture discoloration and reduced strength of the restorative.

Efforts to maintain the mixture's proper moisture content during both use and storage have been met with limited success. One example is described in U.S. Pat. No. 4,180,159 issued Dec. 25, 1979 to Tanaka which teaches a tray assembly for mixing the porcelain material and subsequently maintaining its moisture content. The tray assembly includes a receptacle for mixing and supporting the mixture and an underlying reservoir for storage of water or other liquids. One end of an elongated wick is immersed within the liquid and the opposite end of the wick is disposed in the receptacle and in contact with the product therein. While the liquid is, in fact, drawn via the wick from the reservoir to the mixture, the invention of Tanaka has been criticized for failing to provide sufficient amounts of water to the substrate. This is probably due to the relatively small portion of the wick end which contacts the mixture or perhaps due to restricted liquid flow when hardened mixture residue accumulates on the wick tip causing blockage.

Another earlier invention described in U.S. Pat. No. 3,966,094 issued Jun. 29, 1976 to Sheppard teaches an apparatus having a porous working surface for supporting a castable material again disposed above a reservoir filled with liquid. A flow of liquid is maintained from the reservoir through the porous working surface to the mixture through hydrostatic pressure as a function of liquid elevation within one or more wells. Despite the potentially large amount of water which can be stored in the Sheppard device, once water elevation ceases to make contact with the working surface, moisture loss from the mixture can not be prevented. Moreover, as the water level within the reservoir decreases due to evaporation, the hydrostatic pressure changes resulting in an inconsistent flow rate to the substrate. Accordingly, water level must be frequently checked and maintained to avoid substrate moisture depletion or supersaturation. It is also worth noting that the Sheppard device is not equipped with a lid and is not, therefore, intended for more long term storage of the porcelain mix.

It is clear that a significant need exists for a solution to the shortcomings and limitations of the above described inventions as well as those of other prior art efforts attempting to control moisture content in the dental porcelain mix. The subject invention substantially obviates the problems associated with the prior art by providing a means for regulating moisture content within the substrate mix during both use and storage. Liquid flow to the mix is kept relatively constant over time by exploiting the capillary action inherent in both the subject device and in the mixture itself.

SUMMARY OF THE INVENTION

The subject invention more specifically relates to a mixing and storage apparatus for ceramic materials such as dental porcelain, and comprises an open-cell foam pad disposed within a removable micro fine knit fabric sheath. The pad and surrounding sheath are together charged to a mixing and storage vessel which further contains a sufficient volume of water or other liquid suitable for the preparation of a workable ceramic mix. It has surprisingly been discovered that this assembly is capable of maintaining the proper moisture content of the mix during both use and storage without the frequent need for stirring or water replenishment associated with some prior art devices and without the threat of supersaturation of the mix associated with others. Liquid flow to the substrate mix is regulated by the capillary action inherent in the underlying pad which draws liquid from the container to maintain a consistent liquid content in the pad and in the porcelain powder placed on the fabric surface.

It is, therefore, a primary object of the subject invention to provide a mixing and storage apparatus for powdered ceramic materials such as dental porcelain which is capable of maintaining the proper moisture content of the substrate mix during both its use and storage.

Another object of the subject invention is to provide a mixing and storage apparatus for ceramic materials which is capable of maintaining suitable moisture content of the substrate mix without the need for frequent stirring.

It is also an object of the present invention to provide a mixing and storage apparatus for ceramic materials which will not super-saturate the substrate mix nor require frequent replenishment of its water supply.

It is another object of the present invention to provide a mixing and storage apparatus for ceramic materials wherein the body of the container may be color coded for organizational purposes and the lid of the container is clear to permit viewing of the underlying contents.

Still another object of the present invention is to provide a mixing and storage apparatus for ceramic materials having components which are easily separable for cleaning and periodic replacement.

Yet another object of the present invention is to provide a mixing and storage apparatus for ceramic materials that is simple and inexpensive to fabricate.

Other objects and advantages of the present invention will be apparent upon reference to the accompanying description when taken in conjunction with the following drawings.

DETAILED DESCRIPTION OF THE PREFERRED EMBODIMENT

Figure 1:
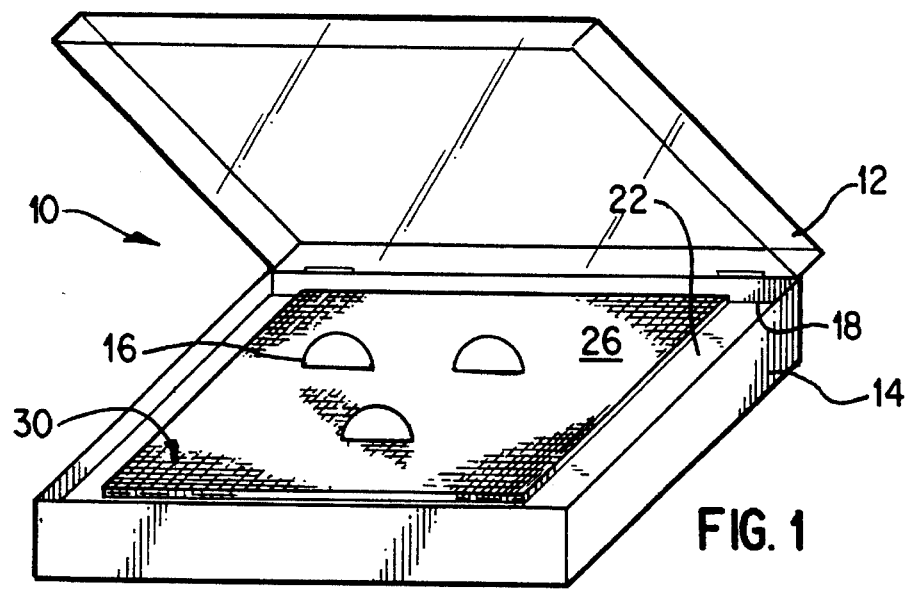
FIG. 1 is a perspective view of the subject mixing and storage apparatus for ceramic materials showing the lid in an open position.

Reference is now made to FIG. 1 in which there is illustrated a perspective view of the preferred embodiment of the subject mixing and storage assembly for ceramic materials comprising, in general, a container 10, liquid-absorbent pad 20 (FIG. 3) and fabric sheath 30.

Figure 2:
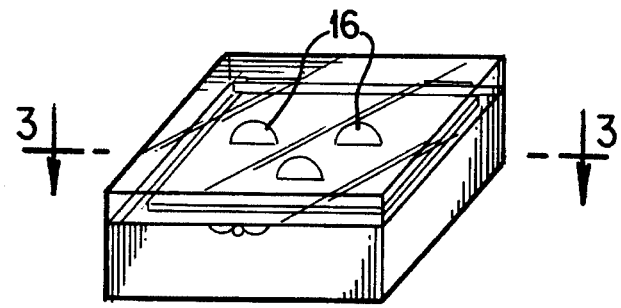
FIG. 2 is a perspective view of the invention of FIG. 1 showing the lid in a closed position.

More particularly, container 10 is preferably fabricated from an injection molded plastic material and is further comprised of a clear or translucent lid portion 12 hingedly attached by conventional means to a colored base portion 14. In the preferred embodiment of the subject invention, both lid 12 and base 14 have planer dimensions of 6"×4"; each further having a third dimension of ¼" and 1", respectively. It may be appreciated, however, that other container sizes and shapes may also be provided and that these specific dimensions are merely illustrative. Coloring of base 14 allows for the color coding of various types of dental porcelain 16 or other ceramic material to be prepared and stored in the assembly. Translucency of lid 12 further allows for the visual inspection of the ceramic material within the container when the lid is closed (FIG. 2) as well as for monitoring of the water level for purposes which will become apparent.

Figure 3:
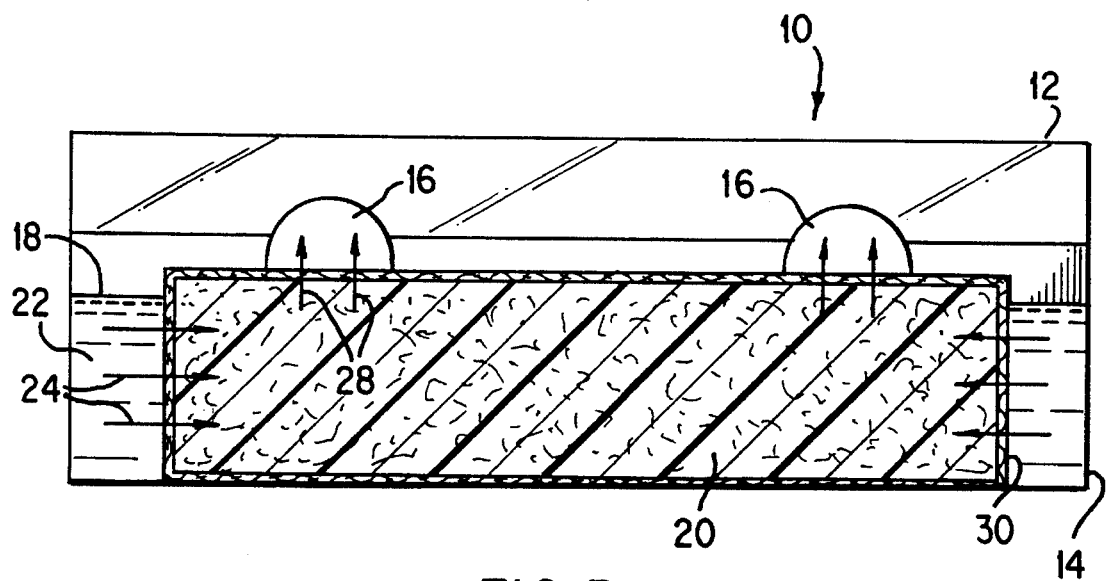
FIG. 3 is a vertical sectional view of the subject invention taken along line A—A of FIG. 2.

Referring now to FIG. 3, it can be observed that pad 20 is generally porous in nature. More specifically, pad 20 is an open-cell foam, preferably constructed of polyether polyurethane or other similar substance having capillary action properties and a density on the order of 1.8. Pad 20 is disposed within fabric sheath 30 which is sewn to relatively similar dimensions so as to provide a snug fit. Sheath 30 is preferably comprised of a micro fine knit fabric having a pore size capable of allowing water or other liquids to pass freely therethrough while preventing passage of porcelain particulate matter.

Pad 20 and surrounding sheath 30 are together placed in base portion 14 of container 10 which further contains a sufficient volume of water or other liquid 18 suitable for the preparation of a workable ceramic mix. Note that the planer dimensions of the pad are less than those of the interior of base 14 such that when pad 20 is positioned in the center of the base a narrow reservoir 22 is formed. Reservoir 22 thus resembles a moat around pad 20 and contains the water or other suitable liquid to be absorbed by the pad. Accordingly, the capillary action inherent in pad 20 withdraws the surrounding liquid 18 from reservoir 22 into itself (as illustrated by horizontal arrows 24) maintaining a saturated state until the contents of reservoir 22 are depleted. It can thus be appreciated that a constant flow of liquid 18 is provided to the overlying sheath 30 and, most importantly, to its top surface area 26. When porcelain powder is placed on surface area 26 of sheath 30, liquid 18 is caused to pass through the porous sheath to the substrate powder 16 (as illustrated by vertical arrows 28). It has surprisingly been discovered that sheath 30 thus acts as a membrane through which the precise amount of liquid 18 necessary is passed to yield and maintain a workable mix with the proper moisture content. Furthermore, it has been observed that the subject invention forms a workable mix almost instantaneously upon contact of the powder with the surface 26 of sheath 30, faster than any prior art device heretofore recognized. Still another important aspect of the subject invention is that it forms a workable mix having a higher wetting angle than any prior art device having a planer working surface. This means that, upon contact with the surface 26 of sheath 30, the powdered ceramic material forms a workable mix that "sits up" in a bead-like fashion rather than spreading outwardly to occupy a greater area of surface 26. The advantages of this feature of the subject invention will be readily apparent to those skilled in the art of fabricating dental restoratives, for example. One immediately apparent advantage is that the mix will not tend to run off of sheath 30 even when the subject device is tilted away from the horizontal plane. Together, container 10, pad 20 and sheath 30 provide a chemically inert assembly capable of regulating the moisture content of the mix by preventing super-saturation and replenishing liquid lost as a result of evaporation.

METHOD OF USE

In practice, the subject assembly for the preparation and storage of dental porcelain is used by inserting pad 20 into sheath 30 and then placing both into base 14 of container 10. With lid 12 in the open position (FIG. 1), the assembly is submerged in the distilled water or other desired liquid 18 while gently pumping the pad with the fingers causing the evacuation of air within the pad and replacement with liquid 18. When all air is gone, the entire assembly is removed from the sink or other vessel containing liquid 18. Base 14 is then drained to approximately 75% capacity to reduce the chance of spillage during handling of the device. Frequently, air bubbles trapped between pad 20 and sheath 30 will be observed which can inhibit proper passage of the liquid through the sheath 30 membrane. To eliminate these obstructions, a plastic syringe may be utilized to pull the bubbles through the fabric by placing the tip over the bubble and drawing back on the plunger. Sheath 30 is then smoothed if necessary.

The dental porcelain or other ceramic material may then be placed at various locations, in powder form, on the surface 26 of sheath 30. The liquid 18 will then be absorbed through sheath 30 to the dry powder until saturation occurs. Liquid withdrawn from pad 20, in turn, will be simultaneously replenished from the surrounding reservoir supply by the capillary action of the pad. Gentle stirring of the new mix with a wetted natural or synthetic brush should be performed as liquid 18 is absorbed by the porcelain powder 16. Agitation should continue until all air bubbles observed coming to the surface of the mixture are gone. The porcelain is now ready to apply. The subject invention eliminates the need for expensive solutions designed to keep porcelain wet and workable.

It should be appreciated that more than one porcelain mixture may be prepared on pad 20. For example, numerous mixtures of different color shades can be maintained on a single pad; the number of different mixtures being limited only by the surface area available which may be increased or decreased by design. A diagram (not shown) may be created on the surface of lid 12 using a permanent marker to map the colors of porcelain placed at various locations on the pad 20. This map can be amended or removed with an alcohol swab or tissue when necessary.

Once the dental porcelain mixture is prepared, it can either be used immediately to fabricate the dental restoratives or may be stored for later use. Water level in reservoir 22 can be checked visually, through translucent lid 12, on a periodic basis during storage. The above described assembly has been observed to maintain the proper moisture content of the mix for up to four weeks without attention. The rate of evaporation will, of course, vary depending on the relative humidity of the ambient air. The liquid 18 may be replenished and sheath 30 removed and washed with a mild detergent as necessary.

Although the present invention has been described with reference to the particular embodiments herein set forth, it is understood that the present disclosure has been made only by way of example and that numerous changes in details of construction may be resorted to without departing from the spirit and scope of the invention. Thus, the scope of the invention should not be limited by the foregoing specifications, but rather only by the scope of the claims appended hereto.

What is claimed is:

1. A mixing and storage assembly for ceramic materials such as dental porcelain comprising:
   (a) a container; said container having a lid and a base;
   (b) a porous sheath; said sheath being comprised of a micro-fine knit fabric having a pore size capable of allowing liquids to pass through said sheath while preventing passage of the ceramic material; and
   (c) a foam pad disposed within said sheath; said pad and said sheath being further disposed within said container;
   whereby a liquid may be charged to said container, absorbed by said pad and diffused through said sheath to the ceramic material placed on the top surface of said sheath, thereby creating a workable mixture.

2. The mixing and storage assembly of claim 1 wherein said pad is capable of transporting water by capillary action to the ceramic mix placed on the surface of said sheath.

3. The mixing and storage assembly of claim 2, wherein said pad is comprised of an open-cell foam of polyether polyurethane.

4. The mixing and storage assembly of claim 1 wherein said pad is comprised of an open-cell foam of polyether polyurethane.

5. A method of forming a workable ceramic mix, such as from dental porcelain, comprising the steps of:
   (a) introducing a liquid into a mixing assembly consisting of:
      (1) a container; said container having a lid and a base;
      (2) a foam pad disposed within said base of said container;
      (3) a porous sheath surrounding said pad, said sheath being comprised of a micro fine knit fabric having a pore size capable of allowing said liquid to pass to and from said pad;
   (b) placing an amount of dry ceramic mix onto the surface of said sheath; said sheath being capable of preventing said ceramic mix from passing through said sheath; and
   (c) permitting said liquid to diffuse through said sheath to said dry ceramic mix, thereby producing a workable mixture.

6. A mixing and storage assembly for ceramic materials such as dental porcelain, comprising:
   (a) a container, said container having a lid and a base;
   (b) a foam pad disposed within said base of said container such that a reservoir is between said pad and at least one of the interior walls of said base to receive water therein; and
   (c) a porous sheath comprised of a micro-fine knit fabric having a pore size capable of allowing liquids to pass through said sheath while preventing passage of the ceramic material; said sheath being completely disposed around said pad and conforming to the shape of said pad;
   whereby a liquid may be charged to said reservoir and absorbed by said pad through said porous sheath and diffused through said sheath to ceramic material placed on the top surface of said sheath thereby creating a workable mix.

7. The mixing and storage assembly of claim 6 wherein said pad is capable of transporting water by capillary action to the ceramic mix placed on the surface of said sheath.

8. The mixing and storage assembly of claim 7, wherein said pad is comprised of an open-cell foam of polyether polyurethane.

9. The mixing and storage assembly of claim 6 wherein said pad is comprised of an open-cell foam of polyether polyurethane.

10. The mixing and storage assembly of claim 6 wherein said pad is capable of transporting water by capillary action to the ceramic mix placed on the surface of said sheath.

11. The mixing and storage assembly of claim 10 wherein said pad is comprised of an open-cell foam of polyether polyurethane.

12. The mixing and storage assembly of claim 6 wherein said pad is comprised of an open-cell foam of polyether polyurethane.

* * * * *